US005993820A

United States Patent [19]
Bagdasarian et al.

[11] Patent Number: 5,993,820
[45] Date of Patent: Nov. 30, 1999

[54] CHIMERIC LTB VACCINES

[75] Inventors: Michael Bagdasarian, Haslett; James Ireland, East Lansing, both of Mich.

[73] Assignee: Michigan State University, East Lansing, Mich.

[21] Appl. No.: 08/747,410

[22] Filed: Nov. 12, 1996

[51] Int. Cl.$^6$ .................. A61K 39/00; A61K 39/385; C07K 1/00
[52] U.S. Cl. .................. 424/192.1; 424/195.11; 424/198.1; 530/350
[58] Field of Search ............ 424/192.1, 195.11, 424/198.1; 530/350

[56] References Cited

U.S. PATENT DOCUMENTS

| | | |
|---|---|---|
| 4,710,463 | 12/1987 | Murray . |
| 4,761,372 | 8/1988 | Maas et al. . |
| 5,241,053 | 8/1993 | Fujisawa et al. . |
| 5,580,563 | 12/1996 | Tam . |
| 5,589,384 | 12/1996 | Lipscombe et al. . |

FOREIGN PATENT DOCUMENTS

| | | |
|---|---|---|
| 0372928 | 6/1990 | European Pat. Off. . |
| WO 88/00208 | 1/1988 | WIPO . |
| WO 93/22450 | 11/1993 | WIPO . |

OTHER PUBLICATIONS

Dallas, W. et al., "Amino acid sequence homology between cholera toxin and *Escherichia coli* heat–labile toxin," *Nature*, 288: 499–501 (Dec. 4, 1980).
Marcello, A. et al., "Efficient extracellular production of hybrid *E. coli* heat–labile enterotoxin B subunits in a marine vibrio", *FEBS Microbiology Letters*, 117: 47–52 (1994).
Michel, L. et al., "Specificity of the protein secretory apparatus: secretion of the heat–labile enterotoxin B subunit pentamers by different species of Gram–bacteria", *Gene*, 152: 41–45 (1995).
Verlinde, C. et al., "Protein crystallography and infectious diseases", *Protein Science*, 3: 1670–1686 (Jul. 1994).
Hirst, T. et al. "The Phenomenon of Toxin Secretion by Vibrios and Aeromonads", *Experientia* 47:429–431 (1991).
Amin, et al. 1993, *Biochem. Soc. Trans.*, 21:213S, "A new method for the purification of the B subunit (EtxB) of *Escherichia coli* heat–labile enterotoxin".
Azcona–Olivera H., et al. 1992, *Appl. Environm. Microbiol.* 58:169–173, "Generation of antibodies reactive with fumonisins B1, B2 and B3 by using cholera toxin as carrier–adjuvant".
Bäckström, et al., 1994, *Gene*, 149:211–217, "Insertion of a HIV–1–neutralizing epitope in a surface–exposed internal region of the cholera toxin B–subunit".
Bäckström, et al., 1995, *Gene* 165:163–171, "Characterization of an internal permissive site in the cholera toxin B–subunit and insertion of epitopes from human immunodeficiency virus–1, hepatitis B virus and enterotoxigenic *Escherichia coli*".

Beamer, et al. 1972, *Endocrinology* 90:823–827, "Radioimmunoassay of mouse luteinizing and follicle stimulating hormones".
Bindon, et al. 1988, *Proc. Austr. Soc. Reprod. Biol.* 20:28, "Superovulation in pubertal heifers immunized against ovine inhibin purified by monoclonal antibody affinity chromatography".
Brown, et al. 1990, *J. Reprod. Fert.* 90:199–205, "Immunization against recombinant bovine inhibin a–subunit causes increased ovulation rates in gilts".
Burger 1993, *Hum. Reprod.* 8(Supp.2):129–132, "Evidence of a negative feedback role of inhibin in follicle stimulating hormone regulation in women".
Burger 1992, *Reproduc. Med. Rev.* 1:1–20 "Inhibin".
Burger 1988, *J. Clin Endocrinol. Metab.* 66:885–886, "Inhibin: definition and nomenclature including related substances".
Crosa 1980, *Infec. Immunity.* 27:897–902.
Devereaux, et al. 1984, *Nucleic Acids Res.*, 12:387–3905.
Findlay, et al. 1993, *Anim. Reprod. Sci.*, 33:325–343, "Inhibin as a fecundity vaccine".
Forage, et al. 1986, *Proc. Nat'l Acad. Sci., USA*, 83:3091–3095, "Cloning and sequencing of cDNA species coding for subunits of inhibin from bovine follicular fluid".
Forage, et al. 1987, *J. Endocrinol.*, 114–R1–R4, "Immunization against an inhibin subunit produced by recombinant DNA techniques results in increased ovulation rate in sheep".
Fürste, et al. 1986, *Gene*, 48:119–131, "Molecular cloning of the plasmid RP4 primase region in a multi–host–range tacP expression vector".
Glencross, et al. 1994, *J. Reprod. Fertil.*, 100:599–605, "Active immunization of heifers against inhibin: effects on plasma concentrations of gonadotrophins, steroids and ovarian follicular dynamics during prostaglandin–synchronized cycles".
Good, et al. 1995, *Biol. Reprod.*, 53:1478–1488, "Isolation of nine different biologically active molecular variants of bovine follicular fluid inhibin".
Groome, et al. 1993, *J. Immun. Methods* 165:167–176, "Immunoassays for inhibin and its subunits. Further applications of the synthetic peptide approach".
Haq, et al. May 1995, *Science*, 268:714–716, "Oral immunization with a recombinant bacterial antigen produced in transgenic plants".
Henderson, et al. 1989, *Proc. N.Z. Soc. Anim. Prod.*, 49:97–101, "Effect of active immunization with follicular fluid on ovulation rates in Romney ewes".

(List continued on next page.)

*Primary Examiner*—Anthony O. Caputa
*Assistant Examiner*—Mark Navarro
*Attorney, Agent, or Firm*—Merchant & Gould

[57] ABSTRACT

A chimeric protein formed of a small peptide antigen inserted into an exposed surface region of the B subunit of heat-labile enterotoxin of *E. coli* useful as an immunogenic vaccine composition.

21 Claims, 11 Drawing Sheets

OTHER PUBLICATIONS

Hirabayashi, et al. 1990, Vaccine, 8:243–248, "Comparison of intranasal inoculation of influenza HA vaccine combined with cholera toxin B subunit with oral or parenteral vaccination".

Holmgren, J. 1973, Infection and Immunity 8:851–859, "Comparison of the tissue receptors for Vibrio cholerae and Escherichia coli enterotoxins by means of gangliosides and natural cholera toxoid".

Hunter, et al. 1962, Nature, 194:495–496, "Preparation of Iodine–131 Labeled Human Growth Hormone of High Specific Activity".

Ireland, et al. 1994, Biol. Reprod., 50:1265–1276, "Alterations in amounts of different forms of inhibin during follicular atresia".

Ireland, et al. 1992, Biol. Reprod. 47:746–50, "Immunoneutralization of Inhibin Suppresses Reproduction in Female Mink".

Jacob, et al. 1984, EMBO J., 3(12):2889–2893, "Neutralization of heat–labile enterotoxin of E. coli by antibodies to synthetic peptides derived from the B–subunit of cholera toxin".

Jacob, et al. 1985, EMBO J., 4:3339–3343, "Priming immunization against cholera toxin and E. coli heat–labile toxin by a cholera short peptide–β–galactosidase hybrid synthesized in E. coli".

Janda, et al. 1988, Clin. Microb. Rev. 1:245–267, "Current perspectives on the epidemiology and pathogenenesis of clinically significant Vibrio spp".

Kaneko, et al. 1995, Biol. Reprod., 53:931–939, "Immunoneutralization of inhibin and estradiol during the follicular phase of the estrous cycle in cows".

Kim, et al. 1991, Int. J. Biochem. 23(11):1307–1313, "Expression of a bovine inhibin β subunit in Escherichia coli".

King, et al. 1993, J. Anim. Sci., 71:975–982, "Ovulatory and endocrine responses after active immunization of gilts against a synthetic fragment of bovine inhibin".

Klipstein, et al. 1983, J. Infect. Dis. 137:318–326, "Vaccine for enterotoxigenic Escherichia coli based on synthetic heat–stable toxin cross–linked to the B–subunit of heat–labile toxin".

Kovacic, et al. 1972, Endocrinology, 91:910–915, "Alterations in serum FSH/LH ratios in relation to the estrous cycle, pseudopregnancy, and gonadectomy in the mouse".

Kusina, et al. 1995, Biol. Reprod., 52:878–884, "Effects of passive immunization of ewes against an inhibin–peptide on gonadotropin levels, ovulation rate and prolificacy".

Leece, et al. 1992, J. Gen. microbiol. 138:719–724, "Expression of the B subunit of Escherichia coli heat–labile enterotoxin in a marine Vibrio and in a mutant that is pleiotropically defective in the secretion of extracellular proteins".

Lipscombe, et al. 1991, Molec. Microbiol. 5:1385–1392, "Intranasal immunization using the B subunit of the Escherichia coli heat–labile enterotoxin fused to an epitope of Bordetella pertussis P69 epitope".

Martin, et al. 1991, Biol. Reprod., 45:73–77, "Immunoneutralization of inhibin modifies hormone secretion and sperm production in bulls".

Mason, et al. Sep. 1995, TIBTECH, 13:388–392, "Transgenic plants as vaccine production systems".

Matsudaria, P. 1987, J. Biol. Chem. 262:10035–10038, "Sequence from picomole quantities of proteins electroblotted onto polyvinylidene difluoride membranes".

Mitraki, et al. 1989, Biotechnology 7:690–697, "Protein folding intermediates and inclusion body formation".

Miyamoto, et al. 1985, Biochem Biophys. Res. Commun. 129:396–403, "Isolation of porcine follicular fluid inhibin of 32 kDaltons".

Mizumachi, et al. 1990, Endocrinology, 126:1058–1063, "Superovulation of ewes immunized against human recombinat inhibin α subunit associated with increased pre–and postovulatory follicle stimulating hormone levels".

Murdoch 1994, Life Sciences, 55:1871–1886, "Immunoregulation of mammalian fertility".

Nashar, et al. 1993, Vaccine 11(2):235–240, "Current progress in the development of the B–subunits of cholera toxin and Escherichia coli heat–labile enterotoxin as carriers for the oral delivery of heterologous antigens and epitopes".

O'Shea, et al. 1987, Proc. Aust. Soc. Reprod. Biol., 19:54, "Immunization of Booroola ewes with fecundin or an inhibin–enriched preparation".

Richter, et al. 1996, J. Travel Med., 3:52–56, "Transgenic Plants Created for Oral Immunization Against Diarrheal Diseases".

Rivier, et al. 1989, Endocrinology, 125(1):125–157, "Immunoneutralization of endogenous inhibin modifies hormone secretion and ovulation rate in the rat".

Rivier, et al. 1991, Endocrinology, 128:1548–1554, "Effect of recombinant inhibin on leutinizing hormone and follicle–stimulating hormone secretion in the rat".

Sagar, et al. 1989, J. Pept. Protein Res., 33:452–456, "Antigenic sites on ribonuclease A. Synthetic peptides corresponding to the sites 37–42 and 83–88 on ribonuclease A show immunogenicity".

Saito, et al. 1989, Endocrinology, 125(2):898–905, "Synthetic peptide segments of inhibinα–and β–subunits: preparation and characterization of polyclonal antibodies".

Sanchez, et al. Jan. 1989, Proc. Nat'l. Acad. Sci. USA, 86:481–485, "Recombinant system for overexpression of cholera toxin B subunit in Vibrio cholerae as a basis for vaccine development".

Sander, et al. 1991, J. Endocrinology, 130:297–303, "Ovulation rate, follicle population and FSH levels in cyclic rats after administration of an inhibin–neutralizing antiserum".

Sandkvist, et al. 1987, J. Bacteriol., 169:4570–4576, "Alterations at the carboxyl terminus change assembly and secretion properties of the B–subunit of Escherichia coli heat–labile enterotoxin".

Sanger, et al. 1977, Proc. Nat'l. Acad. Sci. USA, 74:5463–5467, "DNA sequencing with chain–terminating inhibitors".

Sayers, et al. 1988, Nucleic Acids Res., 16:791–802, "5'–3'Exonucleases in Phosphorothioate–based oligonucleotide–directed mutageneis".

Scanlon, et al. 1993, J. Reprod. Fert., 97:213–222, "Active immunization of heifers against a synthetic fragment of bovine inhibin".

Scarramuzzi, et al. 1993, Immun. Cell Biol., 71:489–499, "Immunological approaches to fertility regulation in domestic livestock".

Schanbacher 1991, J. Anim. Sci., 69:252–257, "Pituitary and testicular responses of beef buls to active immunization against inhibin alpha".

Scott, et al. 1990, Science, 149:386–390, "Searching for Peptide Ligands with an Epitope Library".

Sixma, et al. May 1991, Nature, 351:371–377, Crystal Structure of a cholera toxin–related heat–labile enterotoxin from E. coli.

Sixma, et al. 1993, *J. Mol. Biol.,* 230:890–918, "Refined Structure of *Escherichia coli* Heat–labile Enterotoxin, a Close Relative of Cholera Toxin".

Spangler, B. D. 1992, *Microb. Rev.* 56:622–647, "Structure and function of cholera toxin and the related *Escherichia coli* heat–labile enterotoxin."

Svennerholm, et al. 1978, *Curr. Microbiol.,* 1:19–27, "identification of *Escherichia coli* heat–labile enterotoxin by means of ganglioside immunosorbent assay (GMI–ELISA) procedure".

Towbin, et al. 1979, *Proc. Natl. Acad. Sci. U.S.A.,* 76(9):4350–4354, "Electrophoretic transfer of protein from polycrylamide gels to nitrocellulose sheets: procedure and some applications."

Voglmayr, et al. 1990, *Biol. Reprod.* 42:81–86, "Immunization of rams against human recombinate inhibin α–subunit delays, augments, and extends season–related increase in blood gonadotropin levels".

Warburg, et al. 1942, *Biochem.* 310:384, "Absorptivities in protein estimation".

Wrathall, et al. 1990, *J. Endocrinol.* 124:167–176, "Inhibin immunoneutralization by antibodies raised against synthetic peptide sequences of inhibin α subunit: effects on gonadotrophin concentrations and ovulation rate in sheep".

Wrathall, et al. 1992, *J. Reprod. Fertil.* 95:175–182, "Effects of active immunization against a synthetic peptide sequence of inhibin α subunit on plasma gonadotrophin and concentration, ovulation rate and lambing rate in ewes".

Yamamoto, et al. 1984, *J. Biol. Chem,* 259:5037–5044.

Christophe et al (Protein Sci. vol. 3 1994 pp. 1670–1686).

Geary et al (Vaccine vol. 14 No. 13 Sep. 1996 pp. 1273–1279).

FIG. 2A
Probed with
Anti-EtxB

FIG. 2B
Probed with
Anti-$\alpha_C^{1-26}$bINH kDa | Etx $\alpha_C^{1-14}$
m p m p Etx $\alpha_C^{1-14}$
m p m p

68 —

29 —

14 —

6 —

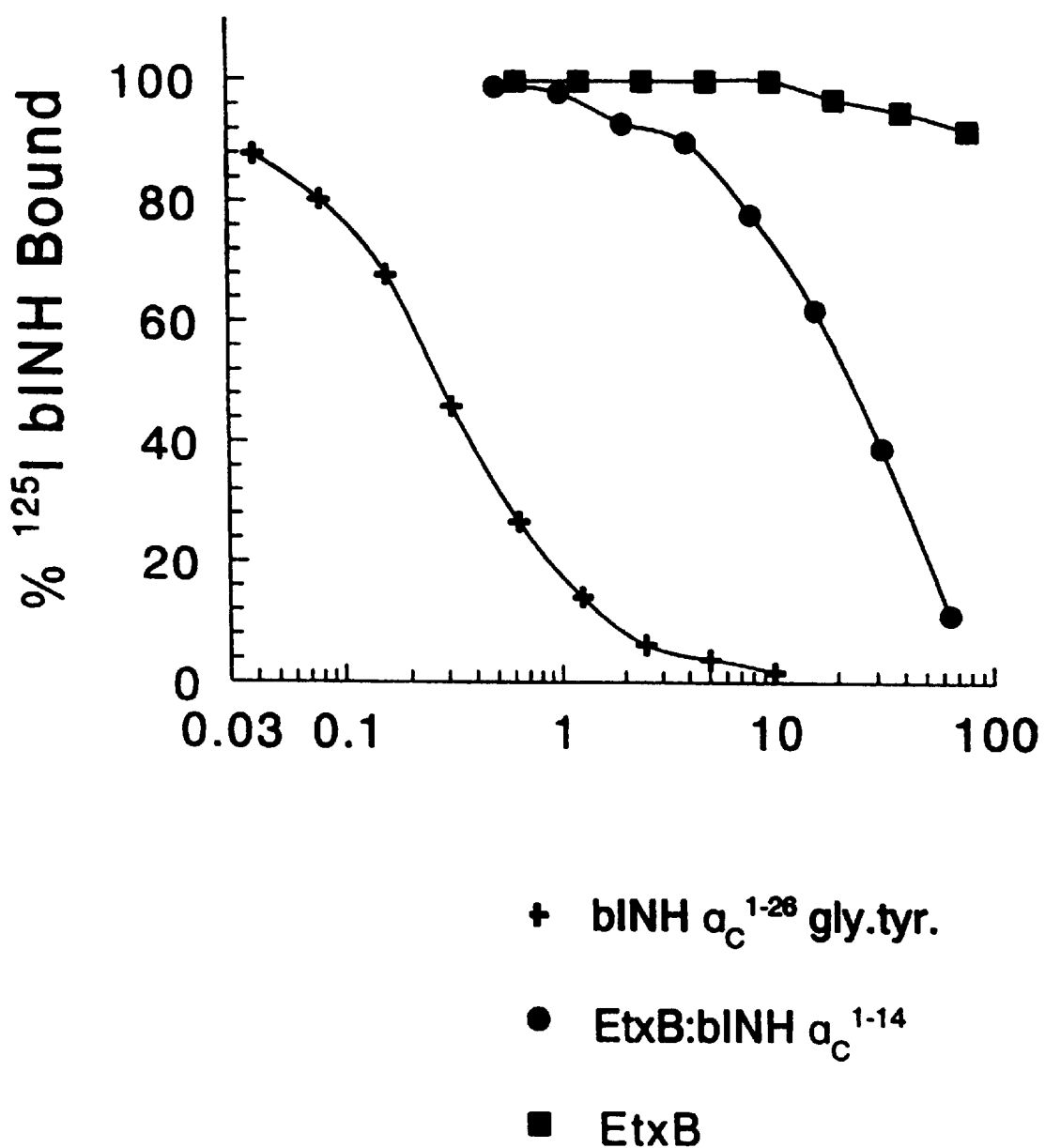

FIG. 4

+ bINH $a_c^{1-26}$ gly.tyr.

● EtxB:bINH $a_c^{1-14}$

■ EtxB (y-axis: % $^{125}$I bINH Bound; x-axis: 0.03 to 100)

FIG. 6A

Passive Immunization

Legend:
- □ Pre
- ▨ Anti-EtxB:bINH $a_c^{1-14}$

Y-axis: Absorbance ($A_{490}$), ranging 0.00 to 0.50
X-axis: Number of doses (1 Dose, 2 Doses)

FIG. 6B

Passive Immunization

□ Pre
▨ Anti-EtxB:bINH $\alpha_c^{1-14}$

Serum FSH (ng/ml)

Serum LH (ng/ml)

1 Dose    2 Doses
Number of Doses

Immunization with monomeric EtxB:bINHα$_C^{1-14}$ with Freund's

A. EtxB Ab titer
B. Inhibin Ab titer
C. FSH
D. LH

FIG. 9

```
        10                    30                    50
         .                     .                     .
AATTCGGGATGAATTATGAATAAAGTAAAATTTTATGTTTTATTTACGGCGTTACTATCC
TTAAGCCCTACTTAATACTTATTTCATTTTAAAATACAAAATAAATGCCGCAATGATAGG
                    MetAsnLysValLysPheTyrValLeuPheThrAlaLeuLeuSer 70                    90                   110
         .                     .    ┌─── α1 ───┐.
TCTCTATGTGCACACGGAGCTCCTCAGTCTATTACAGAACTATGTTCGGAATATCACAAC
AGAGATACACGTGTGCCTCGAGGAGTCAGATAATGTCTTGATACAAGCCTTATAGTGTTG
SerLeuCysAlaHisGlyAlaProGlnSerIleThrGluLeuCysSerGluTyrHisAsn
                    1                                  10

130                   150                   170      StuI
┌──── . β1 ───.──┐    .    ┌─ . β2 ──┐            StuI CT
ACACAAATATATACGATAAATGACAAGATACTATCATATACGGAATCGATGGCAGGCAAA
TGTGTTTATATATGCTATTTACTGTTCTATGATAGTATATGCCTTAGCTACCGTCCGTTT
ThrGlnIleTyrThrIleAsnAspLysIleLeuSerTyrThrGluSerMetAlaGlyLys
              20                                  30

190                   210                   230
┌Mut-prm.┐→ β3 ───.─┐    .     ┌─. β4 ───┐.         SmaI
AGAGAAATGGTTATCATTACATTTAAGAGCGGCGCAACATTTCAGGTCGAAGTCCCGGGC
TCTCTTTACCAATAGTAATGTAAATTCTCGCCGCGTTGTAAAGTCCAGCTTCAGGGCCCG
ArgGluMetValIleIleThrPheLysSerGlyAlaThrPheGlnValGluValProGly
                                                      50

250                   270                   290
         .               ┌──────.───── . α2 ──.─────.
AGTCAACATATAGACTCCCAAAAAAAAGCCATTGAAAGGATGAAGGACACATTAAGAATC
TCAGTTGTATATCTGAGGGTTTTTTTTCGGTAACTTTCCTACTTCCTGTGTAATTCTTAG
SerGlnHisIleAspSerGlnLysLysAlaIleGluArgMetLysAspThrLeuArgIle
                    60                                  70

310                   330                   350
─────────┐    .    ┌────.─ β5 ──.─┐    .           ┌
ACATATCTGACCGAGACCAAAATTGATAAATTATGTGTATGGAATAATAAAACCCCCAAT
TGTATAGACTGGCTCTGGTTTTAACTATTTAATACACATACCTTATTATTTTGGGGGTTA
ThrTyrLeuThrGluThrLysIleAspLysLeuCysValTrpAsnAsnLysThrProAsn
              80                                  90
```

FIG. 9 (Cont'd)

```
            370                    390                      410
    ──  B6    .  ─────────  .  ──┐ SpeI       .           .          .
   TCAATTGCGGCAATCAGTATGGAAAACTAGTTTGCTTTAAAAGCATGTCTAATGCTAGGA
   AGTTAACGCCGTTAGTCATACCTTTTGATCAAACGAAATTTTCGTACAGATTACGATCCT
   SerIleAlaAlaIleSerMetGluAsnEnd
                    100

430                    450                      470
             .          .           .           .            .         .
   ACCTATATAACAACTACTGTACTTATACTAATGAGCCTTATGCTGCATTTGAAAAGGCGG
   TGGATATATTGTTGATGACATGAATATGATTACTCGGAATACGACGTAAACTTTTCCGCC 490                    510                      530
   TAGAGGATGCAATACCGATCCTTAAACTGTAACACTATAACAGCTTCCACTACAGGGAGC
   ATCTCCTACGTTATGGCTAGGAATTTGACATTGTGATATTGTCGAAGGTGATGTCCCTCG 550                    570
              .          .            .          .      .HindIII
   TGTTATAGCAAACAGAAAAAACTAAGCTAGGCTGGGGGGGCAAGCTT
   ACAATATCGTTTGTCTTTTTTGATTCGATCCGACCCCCCCGTTCGAA
```

CHIMERIC LTB VACCINES

FIELD OF THE INVENTION

This invention relates to useful immunogenic molecules formed of the beta subunit of heat-labile enterotoxin (LTB) and an antigenic peptide antigen. More particularly, an antigenic peptide is genetically inserted into an exposed loop region of LTB, resulting in the production of a three dimensional molecule having the inserted antigen exposed on its surface.

BACKGROUND OF THE INVENTION

The development of vaccines based on small antigenic epitopes is hampered by the inability of the small antigen to elicit a good immune response in a host animal. The use of carrier immunogens provides some assistance in the immune response, but often decreases the specific activity and yield of the response against the desired antigen. Methods for conjugation of antigens to carrier agents are costly, and generally utilize hazardous chemicals. Covalent coupling of antigen to a carrier protein is inherently variable, resulting in an antigen with an imprecise structure, compromising vaccine potency. The use of adjuvants also tends to decrease the yield of specific antibodies and can be harmful to the animal host, causing abcesses, skin lesions, and hypersensitivity. These factors are unacceptable for the production of a commercially useful vaccine.

Chimeric molecules formed of large carrier proteins with attached peptide epitopes have been suggested as useful vaccines for small peptide antigens. However, added peptides extending from a three-dimensional protein are generally susceptible to proteolytic degradation. Insertion of an antigenic peptide into an interior portion of a carrier protein may avoid degradation problems, but disruption of the carrier protein's native sequence can alter the carrier's three dimensional structure and thus its function, including its ability to act as an efficient immunogen.

The non-toxic beta subunit of cholera toxin (CTB) and the related B subunit of heat-labile enterotoxin from *E. coli* (LTB) are powerful immunogens that have been suggested for use as carriers of foreign epitopes. In studies testing the activity of CTB, antigenic peptides have been genetically fused to either the N- or C-terminus and tested for activity. These constructs were generally susceptible to rapid proteolytic degradation of the terminally fused peptide. (European Patent Application No: 89312713.4, published Jun. 13, 1990.) In other studies, a CTB-peptide molecule having a 10 amino acid peptide from the HIV-1 gp120 envelope protein substituted for eight amino acids in CTB at positions 56–63 was shown to be resistant from proteolytic degradation as compared with an N-tenninal CTB-peptide product. However, only a detectable response to the substituted gp120 epitope was obtained, and only in some, not all animal hosts. (Bäckström, et al., 1994, *Gene* 149:211–217.)

It is therefore highly desirable to develop an efficient and commercially useful process for producing immunogenic molecules containing antigenic peptide epitopes for use as vaccines, where the immunogenic molecule permits good recognition of the epitope as antigenic without high susceptibility to proteolytic degradation and produces a good immune response against the inserted antigen when administered to a host animal in the absence of adjuvant.

SUMMARY OF THE INVENTION

Chimeric molecules comprising the B subunit of heat-labile enterotoxin (LTB) and an inserted antigenic peptide have been found to display the antigenic epitope in an exposed surface of the LTB molecule without disruption of LTB folding and pentameric assembly and to provide immunogenic molecules useful in generating an immune response against the inserted small antigen. The LTB protein is also referred to as etxB (for enterotoxin B). This protein is encoded by the etxcB gene.

Specific regions of the nucleic acid sequence encoding LTB have been identified as suitable antigen-insertion positions. A nucleic acid construct is produced having a nucleic acid sequence encoding the antigen inserted into the nucleic acid sequence encoding LTB. The insertion is made such that the expressed LTB-antigen fusion protein will include the inserted antigen in an external, exposed loop position. For example, when the antigen's sequence is inserted at approximately nucleotide 237 of etxB without loss of any LTB sequences, the expressed fusion protein displays the antigen on an exposed surface of the folded LTB molecule. At nucleotide 237, the etxB sequence contains a unique Sma I restriction site. In a preferred embodiment of the invention, the antigenic peptide is inserted at the unique Sma I site.

In a most preferred embodiment of the invention, the antigenic fragment is a sequence of the $\alpha C$ subunit of inhibin, the fertility-modulating protein. For example, preferred antigens include $bINH\alpha C^{1-14}$ and $bINH\alpha C^{1-26}$ containing the first fourteen and first 26 N-terminal amino acids of the bovine inhibin alpha-C subunit, respectively. The antigenic sequence is inserted into the LTB molecule by inserting the gene encoding the inhibin fragment into etxB at the unique Sma I restriction site.

Since LTB is a pentameric molecule containing multiple exposed surfaces, the LTB:antigen fusion proteins, when used as vaccines, present multiple antigens for antibody development.

BRIEF DESCRIPTION OF THE FIGURES

FIGS. 2A and 2B are photographs of an SDS-PAGE gel comparing the electrophoretic mobility of wild-type LTB and the LTB-Inhibin fusion protein.

FIG. 3 is a graph showing reactivity of the pentameric form of the fusion protein LTB:$bINH\alpha_C^{1-14}$ in an anti-inhibin radioimmimoassay. The x-axis represents the amounts of protein in each tube. The units of protein amounts are nanograms for the gly.tyr peptide, and micrograms for the other peptides.

FIG. 4 is a graph showing lack of reactivity of the monomeric form of the fusion protein LTB:$bINH\alpha_C^{1-14}$ in an anti-inhibin radioinimunoassay. The x-axis represents the amounts of protein in each tube. The units of protein amounts are nanograms for the gly.tyr peptide, and micrograms for the other peptides.

FIGS. 6A, 6B and 6C are graphs showing anti-inhibin antibody titers in mice immunized with anti-LTB-inhibin fusion protein antibodies.

FIGS. 8A–8D are graphs showing antibody titers in mice actively immunized with pentameric LTB-inhibin fusion protein.

FIG. 9 shows the published sequence encoding LTB.

DETAILED DESCRIPTION OF THE PREFERRED EMBODIMENTS

Figure 1:
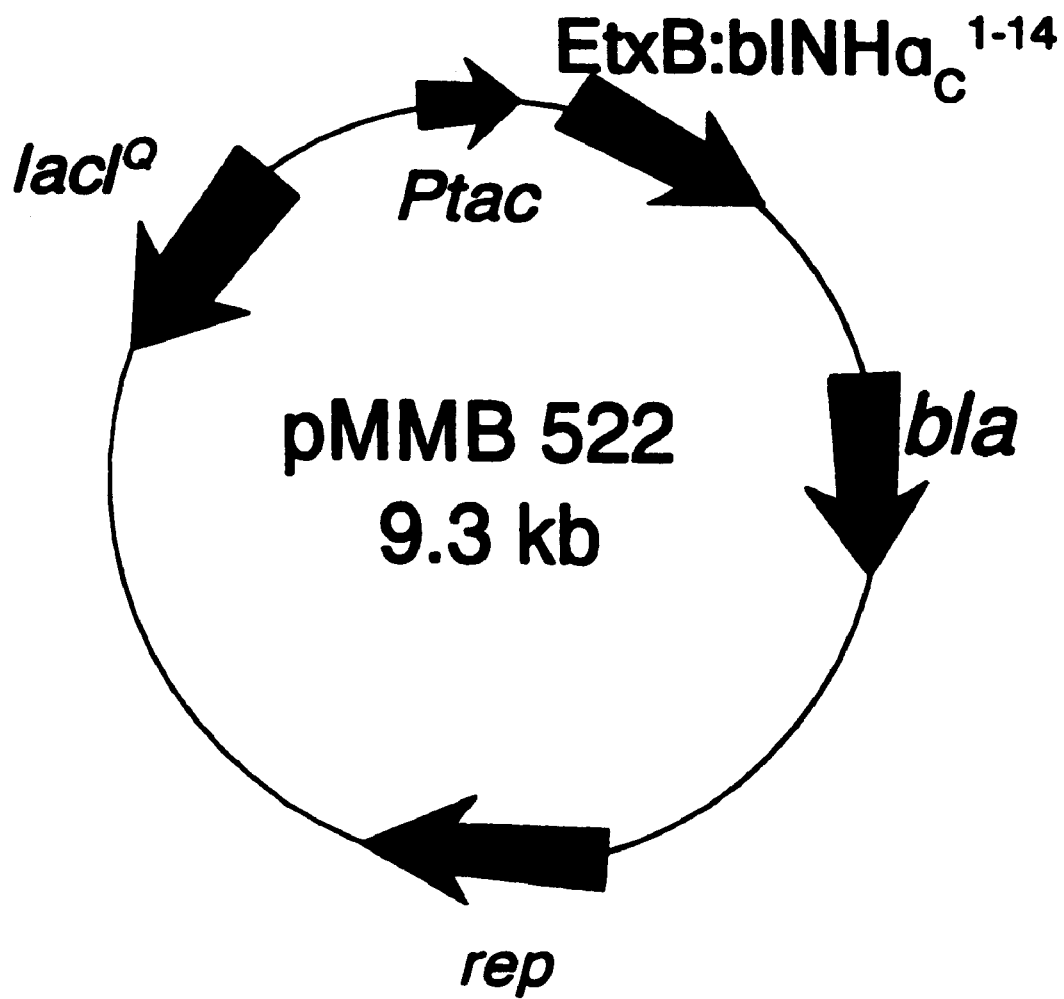
FIG. 1 is a diagram showing the pMMB522 plasmid containing the etxB:$bINH\alpha C^{1-14}$ gene sequences under the control of an IPTG-inducible tac promotor (ptac) from pMMB68, replication determinants of the broad host-range plasmid (rep), the gene encoding β-lactamase (bla), and the gene encoding the lac repressor ($lacl^Q$).

In the preferred embodiments of the invention, an immunogenic carrier molecule, the non-toxic B subunit of the *E. coli* heat-labile ei-terotoxin (LTB), is modified to include an inserted antigenic peptide. The inserted antigenic peptide is positioned in an exposed site of the LTB molecule, e.g., in an external surface of one of the molecule's loops, resulting in the presentation of the antigenic epitope on an exposed surface of the three dimensional chimeric molecule. When used as a vaccine, the chimeric antigen-LTB molecule is effective in eliciting in antibody response against the antigenic peptide in host animals. Vaccination of a host animal with the chimeric antigen-LTB results in the development of specific anti-antigen antibodies in the animal, preferably in the absence of added adjuvant.

LTB

Heat-labile enterotoxin from *E. coli* is a bacterial protein toxin having an $AB_5$ multimer structure. The B pentamer serves a membraine-binding function and the A subunit is needed for enzymatic activity. Structurally, the B subunits are arranged in a donut shape as a highly stable pentamer. The donut shape is formed from five of the identical B subunit monomers arranged symmetrically around a central 5-fold axis with a pore in the middle. For review of the LTB structure and assembly into pentameric form, see Sixma, et al., 1993, *J.Mol. Biol.* 230:890–918, "Refined structure of *Escherichia coli* heat-labile enterotoxin, a close relative of cholera toxin". The crystal structure and three dimensional coordinates of the B subunit are known (Sixma, et al., *Nature* 351:371–377, 1991).

In the $B_5$ pentamer, the identical B subunits interact with themselves, but also have loops that are exposed on the surface of the pentamer. Each subunit takes part in approximately 30 inter-subunit hydrogen bonds and six salt bridges with its two neighbors. Although a large portion of the B subunit's surface area is buried inside the structure of the $AB_5$ or $B_5$ complexes, several loop structures are exposed on the surface of the subunit, and/or on the surface of the associated pentameric complex, as shown by X-ray crystallography. The loops are parts of the secondary structure of the B subunit, which includes a small N-terminal helix, two three-stranded anti-parallel sheets, and a long alpha-helix. Loops in the LTB subunit provide connections between strands and are believed to provide shape to the molecule's binding cavities Analysis of the LTB protein's structure [Seq. ID NO:2] by, for example, interactive computer graphic modeling, identified several domains of the pentamer appropriate for display of inserted epitopes. For example, appropriate insert regions include external loops formed at amino acid positions 10–15; 22–26; 30–37; 41–47; 50–61; 77–82; and 88–94. The sequence of the etxB gene, which encodes each of the identical B subunit proteins, is known [Seq. ID NO:1](Yamamoto, et al., 1984, *J. Biol. Chem.*, 259:5037–5044) and the coding sequences for each of the loops can be determined. The nucleotide residues encoding the loops include positions 109–121; 203–218; 229–260; 310–323, and 343–359. One preferred loop sequence includes nucleic acid residues 229–260, and contains a unique restriction site, SmaI at nucleotide 237. Unique restriction sites can also be engineered into other exposed LTB loops by recombinant DNA technology, permitting ease of insertion of a desired antigen. For example, an external α-helix encoded by etxB nucleic acid residues 92–110 can be engineered to contain a unique Bgl II site at nucleotide 97, by replacing etxB nucleotide 100 with thymine.

Using these unique restriction sites, foreign niucleic acid sequences encoding small peptide antigens from a desired protein may be inserted into a the etxB to form a nucleic acid construct. The small peptide antigen can be a fragment of a larger protein. The foreign sequences encoding a desired antigenic sequence can be inserted so that the reading frame encoding LTB is not disrupted and the peptide antigen is expressed within the LTB sequence. The fusion proteins containing antigenic peptide sequence and the LTB sequence are immunoreactive with antibodies that recognize or bind to the inserted peptide or to an epitope of a protein containing the sequence of the inserted peptide. The immunogenic fusion proteins, or chimeric LTB molecules, can be expressed by methods known for expressing proteins in host cells. On expression of the chimeric LTB molecule, the inserted peptide antigen is expressed on the surface of the molecule and presented for immune response in a host animal. The multimeric structure of LTB allows presentation of multiple antigens on the multiple exposed surfaces of a single pentamer.

Antigens

Antigenic peptides useful in the present invention are generally short amino acid sequences, e.g., approximately 8–30 amino acids, and preferably 10–25 amino acids in length. The peptide is preferably known to be unique to a specific protein of choice, and represents an epitope that is able to induce a desired immune response against the protein target. For example, the antigenic peptide may be known to produce a desired antigenic response when used in another carrier protein/adjuvant system such as co-administration with Fruend's Adjuvant or other immunogen. Alternatively, the peptide antigen may be a portion of a known protein having a particularly unique amino acid sequence distinguishing it from other proteins. These and other techniques for identifying and screening potential antigenic peptides useful in vaccine development are generally known. See, for example, Scott, et al., 1990, *Science* 249:386–390.

Antigenic peptides may be inserted into the LTB molecule by recombinant DNA methods. For example, a synthetic nucleic acid sequence or vector containing the desired nucleic acid sequence to be inserted into etxB is specifically designed to include restriction endonuclease sites matched to a specified endonuclease-cut etxB sequence. Where the etxB contains a single, unique restriction endonuclease site, the antigen's nucleic acid sequence preferably is engineered to include matched restriction sites at both ends of the sequence, so that it can be inserted into the etxB sequence without removal of any etxB nucleotides. Care is taken to match the antigenic nucleic acid sequence to be inserted with the reading frame of the etxB sequence so that normal expression of the encoded LTB and the encoded antigen is achieved.

Insertion of the antigen's nucleic acid sequence and expression of the antigenic peptide does not interfere with normal expression of LTB monomers or with folding of the molecule. Preferably, insertion of the antigenic peptide does not interfere with the association of the LTB monomers into pentameric form. Most preferably, the inserted antigenic peptide does not interfere with LTB 's three dimensional structure, and permits presentation and recognition of the inserted antigen on an exposed surface of the three-dimensional pentameric form of the molecule.

It is contemplated that the compositions and methods of the invention may be limited by the antigenic peptide's amino acid chain length (e.g., no greater than about 30 amino acids), net charge of the inserted amino acid sequence (e.g, less than about 50% highly charged amino acid residues), potentially cross-linking residues, or a density of potentially self-hybridzing nucleic acid sequences. These limitations are generally known and can be recognized by review of the amino acid sequence to be inserted.

It is generally known that a nucleic acid sequence may be modified for enhanced expression in a particular host cell by modifying the codons of the nucleic acid sequence to those more preferred in the specific host cell. Thus, for example, to express the LTB-antigen in *E. coli*, the peptide sequence may be back translated into the nucleotide sequence using the codon frequency found in *E. coli* proteins, as determined by the GCG computer program (Devereaux, et al., 1984, *Nucleic Acids Res.* 12:387–3905) modified as suggested by *E. coli* codon frequencies.

It is generally understood that protein expression in a given host cell may be enhanced by modification of one or more nucleotides in the coding sequence to reduce the number of unique or rare codons. In a preferred embodiment of the invention, the nucleic acid sequence contains one or more codons modified according to the condon frequency preferences for a particular cellular host.

Inhibin Vaccine

Inhibin is a glycoprotein produced by the gonads that selectively suppresses the secretion of follicle stimulating hornone (FSH) from the anterior pituitary gland. A vaccine against inhibin can decrease available inhibin, with a resulting increase in levels of follicle stimulating hormone, and enhanced fertility. Enhanced fertility can be due to enhanced production of sperm or ova. Immunization of animals with bovine inhibin-αC subunit has demonstrated the usefulness of inhibinbased antigens as fertility-enhancing vaccines. However, to date, a practical commercial vaccine has not been produced, at least in part due to the limitations of chemical synthesis, conjugation, and adjuvant toxicity discussed above.

In a most preferred embodiment and exemplary of the invention, the nucleic acid sequence encoding the first 14 N-terminal residues of the antigenic inhibin $\alpha_c$ subunit ($\alpha C^{1-14}$) is inserted into the unique SmaI restriction site of etxB. Alternatively, the nucleic acid sequence encoding the first 26 N-terminal residues ($\alpha C^{1-26}$) is inserted. The chimeric gene is subcloned into a broad-host-range expression vector. The inserted antigen is expressed on the surface of the LTB molecule, such that when the expressed chimeric protein vaccine is injected into host animals, an anti-inhibin response is induced in the animals, reducing inhibin and thereby enhancing fertility in treated animals.

Cellular Hosts

Many known cellular host systems are suitable for expression of the chimeric genes of the invention. For example, non-pathogenic strains such as Vibrio and including *Vibrio anguillarium* are transfected with suitable vectors containing the gene encoding LTB-antigen and express the fusion protein. Suitable vectors for use in Vibrio include pJF 118, as described in Furst, et al, 1986, *Gene* 48:119–131.

Methods of Administration

LTB is a known immunogen. The immunogen of the invention, formed of the intact LTB protein and an inserted antigenic peptide, are administered according to the methods known as effective for the immunogenic administration of proteins such as LTB.

Administration methods include injection of protein compositions to induce effective antibody titers. In a preferred embodiment, the fusion protein of the invention is expressed in edible plants or animals for oral ingestion. This oral delivery method has been described for immunogenic delivery of LTB. See, for example, Mason et.al., 1995, *TIBTECH* 13:388–392, describing oral immunization against LTB via ingestion of transgenic potato tubers expressing LTB antigen.

EXAMPLES

The present invention may be better understood with reference to the following examples. These examples are intended to be representative of specific embodiments of the invention, and are not intended as limiting the scope of the invention.

Examples 1

Analysis of the 3-D Structure of LTB

The B subunit of the *E. Coli* heat-labile enterotoxin (LTB) is a multimeric protein composed of five identical polypeptides of about 11 kDa each. The three-dimensional crystal structure of LTB was analyzed using interactive computer graphic modeling for potential exposed, antigenic regions appropriate for the display of inserted epitopes. Specifically, the structure was analyzed to identify potential sites for insertion of small peptides for purposes of producing potentially antigenic molecules or vaccines.

The protein's structure was examiner with the Biosym modelings program (Biosym Technologies, 1985, Scranton Road, San Diego, Calif.). Domains of the LTB pentamer that are exposed on the surface of the molecule were identified by examination of stereo images. The domains encoding external loops useful for insertion of antigens were selected using the sequence analysis program GCG (Devereaux, et al., 1984, *Nucleic Acids Res.* 12:387–3905). Possible insertion sites were identified as loops in the three-dimensional structure that could potentially tolerate additional amino acids. These loops were also exposed on the surface of the molecule, indicating potential antigen presentation. Aligning the amino acid sequence and then nucleic acid sequence with the identified structural site, potentially useful insertion sites were found.

A potential insertion site is positioned approximately at nucleotide 237, and contains a unique SmaI endonuclease restriction site in the native sequence. A second potential insertion site is positioned at approximately nucleotide 97. While this second site does not contain a unique restriction site in the native sequence, one nucleotide was modified by site-directed mutagenesis to make this site available for direction insertion of foreign oligonucleotides. By replacing adenine at position 100 with thymine, a unique Bgl II restriction site was created at nucleotide 97. In the modified protein encoded by the mutant etxB, Glu-7 is replaced by Asp as shown below:

```
           Wild Type etxB
            (Seq. ID NO:3)
   GCTCCTCAGTCTATTACAGAACTATGTTCGGAATATCAC
80 +---------+---------+---------+-------- 118

1 AlaProGlnSerIleThrGluLeuCysSerGluTyrHis  13
                (Seq. ID NO:4)
```

-continued

```
        Mutant E7D0etxB
         (Seq. ID NO:5)
   GCTCCTCAGTCTATTACAGATCTATGTTCGGAATATCAC
80 +---------+---------+---------+-------- 118

1 AlaProGlnSerIleThrAspLeuCysSerGluTyrHis  13
             (Seq. ID NO:6)
```

A third potential insertion site was created at nucleotide 176 by substitution of adenine nucleotides at positions 179 and 180 with cytosine and thymine nucleotides, respectively. This mutation created a unique StuI site at nucleotides 176–180. This mutation also created a substitution of the The pair of complementary oligonucleotides (Seq. ID No:11) encoding bINHαC$^{1-14}$ (Seq. ID No:12) was inserted into the pMMB68 vector (Sandkvist, et al., 1987, *J Bacteriol.* 169:4570–4576), a broad host-range vector, containing the etxB sequence under the control of the inducible isopropyl-β-D thiogalactopyranoside (IPTG) tac promoter (Sandkvist, et al., 1987, *J: Bacteriol.* 169:4570–4576), digested with SmaI, as shown below. The sequences of the insert are shown in bold type, the nucleotide numbers of the etxB sequences are indicated, and extra nucleotides introduced to maintain the proper reading frame, are underlined. The encoded amino acid sequence is also shown.

```
              230                         240
GTCGAAGTCCCTGGATCCACCCCGCCGCTGCCGTGGCCGTGGTCCCCGGCTGCTCTGGGCAGTCAA
                         (Seq. ID No:11)

VaIGluValProGlySerThrProProLeuProTrpProTrpSerProAlaAlaLeuGlySerGln
                         (Seq. ID No:12)
```

Lys-34 by Leu residue. The resulting mutant LTB subunit was expressed and formed pentamers as did the wild Type LTB

```
          Wild Type etxB
          (Seq. ID NO:7)
     ATGGCAGGCAAAAGAGAAATGGTTATCATTA
170 +---------+---------+---------+200

31 MetAlaGlyLysArgGluMetValIleIle   40
           (Seq. ID NO:8)

Mutant K43L-etxB
          (Seq. ID NO:9)
     ATGGCAGGCCTAAGAGAAATGGTTATCATTA
170 +---------+---------+---------+200

31 MetAlaGlyLeuArgGluMetValIleIle   40
          (Seq. ID NO:10)
```

To create these sequences, wild type LTB was constructed as described in (Sandkvist, et al., 1987, *J. BacterioL.* 169:4570–4576). Site-directed mutagenesis was performed by the method of Eckstein (Sayers, et al., 1988, *Nucleic Acids Res.* 16:791–802). The sequences of the mutant genes obtained were verified by nucleotide sequence determination by di-deoxy sequencing procedures (Sanger, et al., 1977, *Proc. Nat'l. Acad. Sci. USA*, 74:5463–5467).

Example 2

Production of a LTB-Inhibin Fusion Polypeptide

A nucleic acid sequence encoding an immuno-dominant epitope of inhibin, was inserted into the nucleic acid sequence encoding LTB (etxB) at its unique SmaI site. To accomplish the insertion of the sequence, the N-terminal portion of the αC-subunit was back-translated into the nucleotide sequence using the codon frequencies found in *E. coli* proteins, using the GCG program as described above (Devereaux, et al., 1984, *Nucleic Acids Res.* 12:387–3905). Complementary oligonucleotides of this back-translated sequence were chemically synthesized (MSU Macromolecular Structure Facility, Biochem. Dept.) and inserted into etxB in a manner that ensured the continuation of the reading frame after insertion at the SmaI restriction site, as shown in the sequences in the table below.

Recombinant plasmids containing the inhibin subunit sequence were introduced into *E. coli* cells (CB1360, GIBCO BRL, Life Technologies) by standard calcium phosphate transformnation methods. A diagram showing the constructed plasmid (pMMB552) is shown in FIG. 1.

Colonies of transformed *E. Coli* were screened for inhibin and LTB expression by immunoblotting. Colonies were grown on parallel nitrocellulose membrane filters (Schleicher & Schuell), placed on nutrient agar (LB) plates containing ampicillin and IPTG as inducer.

A first filter was blotted with anti-inhibin antibody, and a second filter was blotted with anti-LTB antibodies. Whole cell inhibin immunoblot assays using mink anti-bINHαC$^{1-26}$ gly.tyr antiserum (Ireland, et al., 1994, *Biol. Reprod.* 50:1265–1276) or anti-pentaneric LTB monoclonal antibody 118-8 (Sandkvist, et al., 1987, *J Bacteriol.*, 169:4570–4576) were performed separately on each of the two parallel membranes. Colonies exhibiting both inhibin and LTB immunoreactivity were selected for further DNA sequence screening. DNA from these colonies was isolated by standard methods, cloned into the sequencing vector, M13mp19 and sequenced. The sequence analysis of both DNA strands was done by automated fluorescent sequencing (MSU-DOE-PRL Plant Biochemistry Facility) using ABI catalyst 800 Taq cycle sequencing and the ABI 373A sequencer for the analysis of products. One of the many colonies containing the expected etxB:bINHα$_C$$^{1-14}$ DNA sequence wasidentified as harboring pMMB552 and was retained for continued analysis and development.

To determine if the fusion etxB-inhibin protein exhibited the same pentameric subunit structure as wild type B-subunit, protein produced by *E. coli* cells containing pMMB522 was run on SDS-polyacrylamide gels without denaturation (no boiling of samples) and with denaturation (boiling for 5 minutes).

The electrophoretic mobility of the non-denatured fusion protein was about the same as that of the native LTB. After denaturation, the pentameric form dissociated into monomeric subunits that ran slightly slower than the wild type-B monomers, reflecting their larger size.

Example 3

Expression and Secretion of LTB-Inhibin Fusion Polypeptide in Cellular Host Systems The LTB-Inhibin fusion construct expressing the LTB-inhibin fusion protein, prepared as described for Example 2, was introduced into *Vibrio cholerae* TRH (Sandkvist, et al., 1987, *J: Bacteriol.* 169:4570–4576) and *Vibrio anguilarum* H3 (Crosa, 1980, *Infec. Immunity*, 27:897–902) by conjugative mobilization under conditions sufficient to produce chimeric protein at concentrations greater than 6 mg/I. Conjugation was achieved by making a mixed suspension of the donor strain (*E. coli* CB1360 harboring pMMB552), the helper strain, HB101pRK2013:kanamycin resistant ($Km^R$), and the recipient strains (*E anguillarium* $Rif^R$ or *V cholerae* TRHY 7000: polymyxin resistant, $Pmx^R$)at a 1:1:1 ratio in LB broth in a sterile 1.5 ml eppendorf tube. The suspension mixture was plated on LB medium is a discrete droplet and incubated overnight at 37° C.

The overnight bacterial growth was scraped off the plate and suspended in sterile 0.9% saline solution, then replated on a Rif, $A_p$ selective plate. Selected colonies were individually streaked on fresh LB media (1.5% W/V Bacto-agar plates containing Luria Broth (LB, Difco, Detroit, Mich.) supplemented with 1.5% NaCl and 100 µg/ml amnpicillin (Ap, Sigma, St. Louis, Mo.). Plates were incubated overnight at 30° C. A single colony was picked from the plate, grown in 20 ml LB, and inoculated into one liter LB supplemented with 1.5% NaCl and 100 µg/ml Ap for culture to an absorbance at 650 nm of 0.02–0.05. At $A_{650}$=0.02, IPTG was added to a final concentration of 1.0 mM to induce transcription of etxB. Cultures were harvested 6 or 48 hours after IPTG addition, and medium was saved for analysis and protein purification.

A one ml sample of the cell culture was separated by centrifugation. The separated cells were resuspended in 1.0 ml PBS and broken by sonication with two ten second pulses. The amount of LTB pentamers present in the growth medium and in the lysed cells was determined by GMI ELISA using the methods described in Svennerholm and Holmgren, 1978*, Curr. Microbiol.*, 1:19–27. Briefly, pentameric, but not monomeric LTB binds to galactosyl-N-acetogalactosamninyl-(N-acetylneuraminyl) galactosylglucosylceramide (GM1). To determine if the expressed fusion protein, etxB:bINHα$C^{1-14}$, retained the LTB pentameric structure, the produced protein was tested for its ability to bind ELISA plates coated with GM1 ganglioside (Sigma). Wild type LTB was used as control. The amount of LTB in each sample was estimated from the $ED_{50}$ of the *E. coli* enterotoxin standard curve. The percent LTB in the media was calculated as the amount in the media/the amount in media plus cells×100%.

TABLE 1

| Bacterial | *EtxB* (μg) | | % *EtxB* Pentamers |
|---|---|---|---|
| Strains | Cells | Media | in Media |
| *EtxB*:bINHα$_c^{1-14}$ | | | |
| *V. cholerae* | 148.8 | 16.0 | 9.0 |
| *V. anguillarum* | 92.2 | 91.6 | 50.0 |
| *EtxB* | | | |
| *V. cholerae* | 0.0 | 57.0 | 100.0 |
| *V. anguillarum* | 4.6 | 70.0 | 94.0 |

As shown in Table 1 above, both host cells *V. anguillarum* and *V. cholerae* produced the recombinant fusion protein. Although the total amount of fusion protein produced in each host was similar, more fusion protein was detected in the medium of *V. anguillarum* as compared with *V. cholerae.*

Fusion protein accumulated in the medium of 1 liter cultures was precipitated with ammonium sulfate (65% saturation) according to the methods described in Amin et.al., 1993*, Biochem. Soc. Trans*., 21:213S. The precipitate was recovered by centrifugation (10,000×g, Beckman L-80 ultracentrifuge) for 25 minutes, was redissolved in PBS containing 5% glycerol, and ws dialized against the same buffer at 40° C.

An ion exchange column (CL 6B DEAE-Sepharose, 9.5×1.6 cm, Pharinacia, Piscataway, N.J.) equilibrated with PBS containing 5% glycerol, was used to further purify the fusion protein. An increasing NaCl gradient (137 to 600 mM in PBS-glycerol) was used to elute fractions. An aliquot of each collected fraction was diluted 1:1000 in PBS-Tween containing 0.1% BSA and assayed by GM1 ELISA as described above to detect pentameric fusion protein. Fractions with the highest amount of the fusion protein were pooled, and the protein mass estimated from spectrophotometer readings using the Warburg equation: $A_{280}$=1 for 0.1% protein solution. LTB specific activity was estimated as the amount of GM1-reactivity as determined by the GM1 assay per total protein estimated by spectrophotometer readings.

The fusion protein was eluted as a single peak between 300 and 430 mM of the NaCl gradient. An average of 84.9+/−21.5 mg of the fusion protein was isolated (67+/−11% recovery) with an LTB specific activity of 0.84+/−0.02 per liter.

Protein eluted from the ion exchange column was assessed for purity and molecular weight by SDS-PAGE. Pentameric or heat-disrupted (100° C.) monomeric samples (1.2 to 3.6 μg) of LTB or the fusion protein, LTB:bINHα$_C^{1-14}$ were separated in one dimensional 12% SDS-PAGE in a mini-gel apparatus following the manufacturer's instructions (Mini-Protean II, BioRad). Separated proteins were visualized by Coomassie blue staining and compared with molecular weight markers for estimation of size.

A single major band for each of the pentamneric LTB (39.5±1 kDa) and monomeric LTB (8.9±0.4 kDa) was observed in the stained gels. The major band for each of the pentameric LTB:bINHα$_C^{1-14}$ (41.6±2 kDa) and monomeric LTB:bINHα$_C^{1-14}$ (10.1±0.2 kDa) were larger than the LTB bands, according to the expected size of the insert.

The pentameric or heat-disrupted monomeric fusion protein samples were further analyzed for inhibin and LTB specificity by immunoblotting techniques. Briefly, duplicate samples were electrophoresed in 12% SDS-PAGE and electroeluted onto nitrocellulose membranes, as described above. After blocking with 0.01% Blotto (Food Club, Skokie, Ill.) in TBS for 2 hours, the membrane was washed in Tween-TBS (0.05% Tween-20), and cut to present two replicate membranes for antibody binding.

One of the membranes was incubated with mink anti-bINHα$_{C1-26}$gly.tyr antiserum (1:1000 in TTBS) overnight at room temperature, as described in Ireland et.al., 1994*, Biol. Reprod*., 50:1265–1276. After washing in TTBS (5, 10-minute washes), the membrane was further incubated in 20 ml $^{125}$I-bINHα$_C^{1-26}$gly.tyr (1×10$^6$ cpm/ml in TTBS with 1% gelatin), for competition. The membrane was washed and placed on Xray film (Kodak X-OMAT AR) with a Cronex intensifying screen and exposed for ten days at −80° C.

The second membrane was incubated with a monoclonal anti-LTB antibody (118-8, 1:100 dilution) as described in Sandvikst et.al., 1987, *J Bacteriol.*, 169:4570–4576. Incubation with second antibody goat anti-mouse peroxidase conjugate (Vector) diluted 1:5000 in TTBS was followed by visualization in 0.2% (w/v) 4-chloro-1-napthol (Sigma) in PBS containing 20% methanol and 0.01% $H_2O_2$.

As shown in FIG. 2, the immunoblot assays confirmed LTB:bINHα$_c^{1-14}$ fusion protein was produced having dual inhibin and LTB immunoreactivity. Anti-LTB antibody recognized both wild type LTB and the fusion protein in both monomeric and pentameric forms. Anti-bINHα$_c^{1-26}$gly.tyr antiserum recognized only the monomeric and pentameric forms of the fusion protein, and did not bind the LTB alone. Molecular weight determinations for the immunoreactive proteins were similar for the monomeric (11 kDa, open arrow) and pentameric (45 kDa, shaded arrow) forms as compared with the size estimates obtained from Coomassie blue stained gels.

Inhibin Radioimmunoassay (RIA)

Inhibin immunoactivity in duplicate samples of the fusion protein (0.5–64 μg) in both monomeric and pentameric forms, and in control samples, including bINHα$_c^{1-26}$gly.tyr peptide standards (0.039 ng–10 ng), pentameric and monomeric LTB (0.625 μg–80μg), was determined by radioimmunoassay using mink anti-bINHα$_c^{1-26}$gly.tyr antiserum diluted 1:40,000 in RIA buffer (0.01M NaH$_x$PO$_4$, 0.1M NaCl, 0.025M EDTA, 0.1% NaN$_3$, 0.1% Triton X-100, 0.1%BSA). $^{125}$I-bINHα$_c^{1-26}$gly.tyr (20,000 cpm/tube) was used as tracer. The RIA conditions were as described in Ireland, et al., 1992 Biol. Reprod., 47:746–50; and Good, et al., 1995, Biol. Reprod., 53:1478–1488. Briefly, 200 μl of protein sample, 200 μl mink anti-bINHα$_c^{1-26}$gly.tyr antiserum and 100 μl 125-bINHα$_c^{1-26}$gly.tyr tracer were sequentially added into test tubes and incubated for 16–18 hours at 4° C. The antibody: $^{125}$I-bINHα$_c^{1-26}$gly.tyr complex was incubated for 2 hours with 100 μl Staphylococcus protein A (Staph A; Boehringer Mannheim) diluted 1:50 in RIA buffer at room temperature, followed by the addition of 2 ml/tube PBS (pH 7.4 with 0.025 M EDTA) and centrifugation for 30 minutes at 2,200×g at 4° C. (Beckman GPR centrifuge) to sediment the inhibin-antibody complex. Tubes were decanted and radioactivity in the Staph A:antibody:$^{125}$I-bINHα$_c^{1-26}$gly.tyr complex determined using a MACC Micromedic γ-counter. Inhibin immunoactivity was plotted as percent $^{125}$I-bINHα$_c^{1-26}$gly.tyr tracer bound.

As shown in FIG. 3, the pentameric fusion protein, LTB:bINHα$_c^{1-14}$ reacted with the anti-inhibin antiserum parallel to the reaction of bINHα$_c^{1-26}$gly.tyr peptide. In a separate RIA, monomeric fusion protein did not react with the antiserum (FIG. 4).

Example 4

Passive Immunization of Mice and Rabbits with Anti-EtxB:bINHα$_c^{1-14}$Antiserum Use of the LTB:bINHα$_c^{1-14}$ fusion protein as a fertility vaccine requires that LTB:bINHα$_c^{1-14}$ stimulates production of serum inhibin antibodies when injected into animals, ideally in the absence of adjuvant. As shown above in Example 3, pentameric form of LTB:bINHα$_c^{1-14}$ fusion protein cross-reacted in a parallel fashion with a synthetic bINHα$_c^{1-26}$gly.tyr. peptide during radioimmunoassay (RIA) indicating that bINHα$_c^{1-14}$ peptide is on the hydrophilic surface of the intact, non-denatured molecule. These RIA data imply that the bINHα$_c^{1-14}$ peptide portion of EtxB:bINHα$_c^{1-14}$ is immunogenic, especially since immunogenicity is closely correlated with hydrophilicity (Sagar, et al., 1989 J. Pept. Protein Res. 33:452–456). In addition, bINHα$_c^{1-4}$ peptide was inserted between amino acid 53 and 54 in EtxB a region of LTB known to be highly immunodominant (Jacob, et al., 1984 EMBO J. 3:2889–2893, and 1985 EMBO J. 4:3339–3343).

Animals

Rabbits and mice were maintained by the University Laboratory Animal Resources (ULAR, Michigan State University) in their animal care facilities for the duration of the experiments. All animals were maintained on a 12L: 12D cycle with food and water provided ad libitum.

Treatments

I. Active Immunization

Adult female New Zealand White rabbits of 6–7 kg body weight were purchased from ULAR and housed 1/cage. Purified LTB:bINHα$_c^{1-14}$ fusion protein produced in Vibrio anguillarum as described in Example 3, was mixed with or without Freund's adjuvant and used to actively immunize rabbits. For antigen preparation in Freund's adjuvant, 3 ml LTB:bINHα$_c^{1-14}$ in phosphate buffered saline (PBS-0.01M phosphate buffer, pH 7.4 with 0.15M NaCl) was mixed with an equal volume of Freund's complete (primary injection) or incomplete (boosters) adjuvants (Calbiochem, La Jolla, Calif.) to give a final sample concentration of 100 (primary) or 50 (boosters) μg LTB:bINHα$_c^{1-14}$ per ml. Antigen and adjuvant were mixed in 12×75 mm glass test-tubes and emulsified using a 10 ml syringe with an 18 gauge needle. Mixing was done by suction and expulsion of the antigen and adjuvant through the needle until a stable emulsion was obtained. The emulsion was considered stable when a droplet of emulsion on the surface of the water in a beaker did not disperse when the beaker was shaken. For antigen preparation without Freund's adjuvant, LTB:bINHα$_c^{1-14}$ fusion protein was diluted in PBS to a concentration of 100 (primary) or 10 (boosters) μg LTB:bINHα$_c^{1-14}$ per 0.5 ml (2 ml total volume) and sterilized by expulsion through a 2.2 μm Millex GV sterile filter (Millipore, Bedford, Mass.) attached to a 5 ml syringe into a 15 ml sterile polypropylene tube.

All rabbits were bled from the marginal ear vein before immunization to recover preimmune serum which was used as the negative control. For the adjuvant group (n=3), the primary dose (volume=1 ml) of LTD:bINHα$_c^{1-14}$ was given s.c. in the nape of the neck or in the back at 10 sites (0.1 ml per site) followed by five s.c. boosters at 2-week intervals. For the group immunized without Freund's adjuvant (n=3), the primary dose of LTB:bINHα$_c^{1-14}$ (volume=0.5 ml) was injected i.v. into the marginal ear vein followed by five boosters at 2-week intervals. LTB:BINH injections were performed while restraining rabbits in a towel (ULAR recommendations). To collect blood, rabbits were anesthetized with sodium phenobarbitone (Nembutal, Sigma, St. Louis, Mo.) and blood was removed from a marginal ear vein (5–15 ml) or the heart (100–150 ml) using a 20 or 50 ml syringe with a 20 gauge needle. Serum samples were collected 14 days after each booster for a total of five bleeds per rabbit. Blood samples were incubated at room temperature for 2 hours and then at 4° C. overnight. Serum was separated from clotted blood cells by centrifugation at 1000×g for 30 minutes at 4° C. then stored at –20° C. until assayed by ELISA. Serum from three rabbits with the highest inhibin antibody titer was pooled and used to passively immunize mice.

II. Passive Immunization

Twenty prepubertal male BALB/c mice (25 days old) averaging 12.2±1.4 grams body weight were purchased from Harland Sprague Dawley (Wilmington, Mass.) and housed 5/cage. Rabbit anti-LTB:bINHα$_c^{1-14}$ antiserum generated, as described above, was used to passively immunize mice, and preimmune serum was used as control. Crude anti-LTB:bINHα$_c^{1-14}$ antiserum or preimmune serum was filter-sterilized through a 2.2 μm Millex GV sterile filter attached to a 5 ml syringe and collected into 15 ml sterile polypropylene tubes.

Mice were divided into four groups (5 mice/group). The first two groups were given one 0.5 ml i.p. injection of either rabbit anti-LTB:bINHα$_c^{1-14}$ antiserum or preimmune control serum, whereas the other two groups received two, 0.5 ml i.p. injections of either anti-LTB:bINHα$_c^{1-14}$ or preimmune serum spaced 12 hours apart. After mice were anesthetized with Metofane (Methoxyflurane; Pitman-Moore, Mundelein, Ill.), blood was collected via heart puncture 12 hours after the last injection in each group, serum processed, as described above in Active Immunization, and inhibin antibody titer and concentrations of FSH and LH in serum determined, as described below.

Antibody Titer Determination by ELISA

I. Anti-LTB Antibody Titer

A modification of the GM1 ELISA, described in Svennerholm and Holmgren, 1978, supra, was used to determine anti-LTB antibody titer in serum from actively immunized rabbits (5 bleeds/rabbit). Probind microliter plates (Falcon, Lincoln Park, N.J.) were coated overnight at room temperature with 0.2 μg/well galactosyl-N-acetogalactosaminyl-(N-acetylneuraminyl)-galactosyl glucosylceramide (GM1) in PBS. After washing wells three times with PBS containing 0.05% Tween-20 (PBS-T), non-specific binding sites were blocked by adding 1% BSA (Sigma) in PBS-T to each microwell and incubating for 2 hours at room temperature. Plates were washed and incubated with 100 ng/well partially purified pentameric LTB for 1 hour at room temperature. After another wash, microwells were incubated with serum from actively immunized rabbits diluted 1:5000 in PBS-T containing 0.1% BSA (PBS-T-B) for 1 hour at room temperature. After washing with PBS-T, horseradish peroxidase-labeled goat anti-rabbit IgG diluted 1:5000 (Vector, Burlingame, Calif.) in PBS-T-B was added to each microwell and incubated for 1 hour at room temperature. Color was developed using ortho-phenylenediamine (OPD) in 0.1M citrate buffer, pH 4.5, containing 0.01% $H_2O_2$. After 10 minutes, color development was terminated by adding 3M phosphoric acid. Titer of anti-LTB antibodies in serum was defined as absorbance at 490 nm ($A_{490}$, Bio-Rad microplate reader, Model 3550).

II. Inhibin Antibody Titer

A modified ELISA method, as described in Groome and O'Brien, 1993 *J. Immun. Methods* 165:167–176, was used to estimate titer of anti-inhibin antibodies in serum. Xenobind microliter plates (Xenopore Inc., Hawthrone, N.J.) were covalently coated overnight at room temperature with 1 μg/well bINHα$_c^{1-26}$gly.tyr. peptide or 1 μg/well partially purified bovine inhibin ppbINH, prepared as described in Good, et al., 1995, *Biol. Reprod.*, 53:1478–1488, in PBS as recommended by the manufacturer. After washing wells three times using PBS-T, non-specific binding sites were blocked by incubating wells with 3% gelatin (Bio-Rad) in PBS-T for 2 hours at room temperature. Plates were washed and the coated microwells incubated for 2 hours with serum from actively immunized rabbits or passively immunized mice diluted 1:100 in PBS-T-B. After washing with PBS-T, horseradish peroxidase labeled goat anti-rabbit IgG (Vector, Burlingame, Calif.) diluted 1:5000 in PBS-T-B was added to each microwell and incubated for I hour at room temperature. Microwells were thoroughly washed, color was developed using OPD-$H_2O_2$, and titer of inhibin antibodies in serum was determined, as described in LTB antibody titer.

FSH and LH RIA

I. Iodination and Validation

Concentrations of FSH and LH in serum from passively immunized mice were determined in duplicate samples using rat FSH and LH reagents kindly supplied by the National Institute of Diabetes and Digestive and Kidney Diseases (NIDDK). The chloramine-T method described in Hunter and Greenwood, 1962, *Nature* 194:495–496, was used to radiolabel 5 μg of rFSH (NIDDK-rFSH-I-8) or rLH (NIDDK-rLH-I-9) dissolved in 20 μl PBS in a Nalgene cryovial (Nalge, Rochester, N.Y.). Iodinated rFSH and rLH was stored at 4° C. for use as tracer in each RIA.

The ability of radioiodinated hormone to bind antiserum was determined in duplicate by incubating 50 μl antiserum (NIDDK-anti-rFSH-S-11 or NIDDK-anti-rLH-S-11) diluted 1:1000 to 1:640,000 in assay buffer (0.0095 M $Na_2HPO_4$, 0.014 M $NaH_2PO_4$, 0.15 M NaCl, 0.01 M EDTA, 0.1% $NaN_3$, 0.5% Chicken Egg Albumin, pH 7.2) with 100 μl assay buffer and 50 μl $^{125}$IrFSH or $^{125}$IrLH tracer diluted to 12,000 cpm/tube with assay buffer. Tubes were incubated in the aforementioned buffers for 18 hours at room temperature followed by: 1) precipitation of the bound antibody by incubating tubes with 50 μl/tube of Staphylococcus protein A (Staph A; Boehringer Mannheim) diluted 1:100 in PBS-EDTA (PBS, pH 7.4, 0.025 M EDTA) for 1.5 hours at room temperature; 2) addition of 2 ml/tube PBS-EDTA to wash tubes; and 3) immediate centrifugation for 30 minutes at 2,200×g at 4° C. (Beckman GPR centrifuge) to sediment the Staph A:antibody:tracer complex. The tubes were decanted and radioactivity in the dried pellet determined in a MACC Micromedic γ-counter. Percent binding of tracer to antibody was calculated as:

$$\% \text{ binding} = (\text{average cpm for each dilution}) \times 100 \text{ average total cpm}$$

An antiserum dilution of 1:100,000 resulted in 20% binding of tracer to LH or FSH antibody, thus the 1:100,000 dilution was used in RIA of rFSH or rLH in serum (data not shown).

II. RIA

Mouse FSH and LH cross-react with the NIDDK rat gonadotropin antibodies (Bearner, et al., 1972 *Endocrinology* 90:823–827; Kovacic and Parlow, 1972 *Endocrinology* 91 :910–915). In the present study, several dilutions of BALB/c mouse serum were used to confirm parallelism of mouse serum to the standard curve produced by NIDDK-rat-FSH-RP-2 or NIDDK-rat-LH-RP-3 reference preparations. The standard FSH and LH assay (Parkening, et al., 1980) was miniaturized to reduce the total incubation volume from 600 μl to 200 μl. Duplicate mouse serum samples (5 to 50 μl) diluted to 100 μl in assay buffer were incubated with 50 μl antiserum (1:100,000 in assay buffer, NIDDK-anti-rFSH-S-11 or NIDDK-anti-rLH-S-11) at room temperature for 18 hours. The following day, 50 μl tracer was added at 12,000 cpm/tube and the mixture further incubated at room temperature for 24 hours. This second incubation was followed by precipitation with Staph A as described in Iodination and Validation. Tubes were decanted and the radioactivity in each dried pellet determined in a MACC Micromedic μ-counter. FSH values were expressed in terms of the rat FSH-NIDDK-RP-2 reference standard, whereas LH values were expressed in terms of the rat LH-NIDDK-RP-3 reference standard. Samples were analyzed in a single assay for each hormone. rFSH and rLH assay sensitivities were 0.625 and 0.156 ng/ml and intra-assay coefficients of variation (cv) were 6.3 and 1.6%, respectively. The cross reaction of FSH with LH and of LH with FSH was <2% (per NIDDK guidelines).

Statistics

Results were subjected to ANOVA. Whether significant ($P<0.05$) differences existed between means was determined by Student's t-test.

RESULTS

Active Immunization of Rabbits

Figure 5:
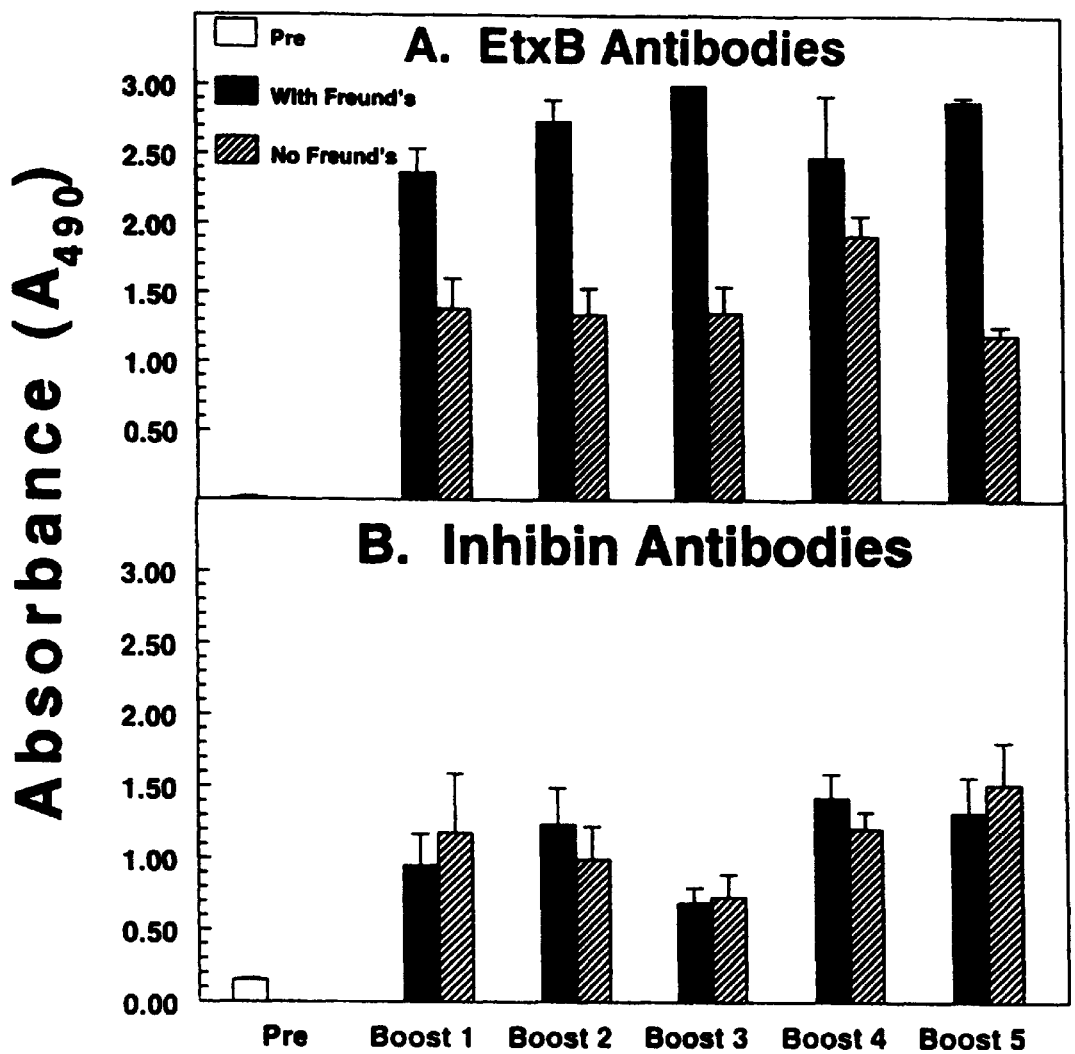
FIGS. 5A and 5B are graphs showing anti-inhibin antibody titers in rabbits immunized with LTB-inhibin fusion protein.

Antibodies were generated to both LTB and $bINH\alpha_c^{1-14}$ components of the $LTB:bINH\alpha_c^{1-14}$ fusion protein in the two groups of rabbits injected with $LTB:bINH\alpha_c^{1-14}$ mixed with or without Freund's adjuvant. Specifically, both LTB and inhibin antibody titers reached a peak after the first booster and stayed elevated for the duration of the experiment, although a transient decrease ($P<0.05$) in the inhibin antibody titer after booster 3 was observed (FIG. 5). In addition, rabbits immunized with $LTB:bINH\alpha_c^{1-14}$ in Freund's adjuvant had anti-LTB antibody titers twice ($P<0.05$) as high as those immunized without Freund's adjuvant. However, anti-inhibin antibody titers were similar between rabbits injected with $LTB:bINH\alpha_c^{1-14}$ mixed with or without Freund's adjuvant.

As shown in FIG. 5, preimmune serum did not bind to LTB and $bINH\alpha_c^{1-26}$gly.tyr. peptide in ELISA. Antibodies generated against the $LTB:bINH\alpha_c^{1-14}$ fusion protein mixed with or without Freund's adjuvant bound to native inhibin but not to preimmune control serum.

Passive Immunization of Mice

I. Inhibin Antibody Titer Following Passive Immunization

The inhibin antibody titer was higher ($P<0.05$) in mice that received one injection of anti-$LTB:bINH\alpha_c^{1-14}$ antiserum compared with preimmune controls (FIG. 6A). Inhibin antibody titer was also higher ($P<0.05$) in mice that received two injections of anti-$LTB:bINH\alpha_c^{1-14}$ antiserum than those that received a single anti-$LTD:bINH\alpha_c^{1-14}$ injection or preimmune controls (FIG. 6A).

II. Serum Concentrations of FSH and LH

Administration of two injections of anti-$LTB:bINH\alpha_c^{1-14}$ antiserum resulted in a nearly two-fold increase ($P<0.05$) in plasma concentrations of FSH compared with preimmune controls (FIG. 6B). In contrast, concentrations of serum LH were similar ($P>0.1$) for anti-$LTB:bINH\alpha_c^{1-14}$ treated and preimmune control mice (FIG. 6C).

The results of this study demonstrate that:

1) Immunization with $LTB:bINH\alpha_c^{1-14}$ fusion protein stimulated production of anti-$bINH\alpha_c^{1-14}$ antibodies when injected into rabbits with or without Freund's adjuvant;

2) Anti-$bINH\alpha_c^{1-14}$ antibodies stimulated by immunization with $LTB:bINH\alpha_c^{1-14}$ bound to native inhibin; and, 3) Anti-$bINH\alpha_c^{1-14}$ antibodies stimulated by immunization with $LTB:bINH\alpha_c^{1-14}$ effectively neutralized endogenous inhibin in host animals.

Example 5

Active Immunization of Mice with $EtxB:bINH\alpha_c^{1-14}$

Animals

Mice were maintained by the University Laboratory Animal Resources (ULAR, Michigan State University) in their animal care facilities for the duration of the experiment. Male BALB/c mice (25 days old) were purchased from Harland Sprague Dawley (Wilmington, Mass.) and housed 5/cage, maintained on a 12L:12D cycle, and provided with food and water ad libitum.

Immunization Protocol

After Metofane anesthesia (Methoxyflurane; Pitman-Moore, Mundelein, Ill.), mice were bled by gently inserting a heparinized microhematocrit capillary tube (200 $\mu$l, Fisher, Pittsburg, Pa.) into the orbital sinus of the mouse. After filling the microhematocrit capillary tube with blood, the tube was sealed using hemato-seal tube sealing compound (Fisher, Pittsburg, Pa.) then centrifuged for 5 minutes at full speed to recover preimmune plasma.

Purified $LTB:bINH\alpha_c^{1-14}$ and LTB proteins were used to actively immunize mice. Beginning at 26 days of age, male mice (n=5/group) were injected subcutaneously (s.c.) over a 10-week period at either 2-or 4-week intervals with two doses (10 or 40 pg) of $LTB:bINH\alpha_c^{1-14}$ fusion protein or one dose (40 $\mu$g) wild type LTB (controls). Each immunogen was injected in its pentameric or heat-disrupted monomeric form mixed with or without Freund's adjuvant. A group of ten untreated mice served as additional controls. To prepare the monomeric form, 500 $\mu$l aliquots of $LTB:bINH\alpha_c^{1-14}$ or LTB were heated in a heating block (100° C. for 15 minutes) then left to cool at room temperature for 15 minutes before preparation for immunization. Henceforth, sample preparations for pentameric and monomeric $LTB:bINH\alpha_c^{1-14}$ and EtxB are similar.

For antigen preparation in Freund's adjuvant, 400 or 800 $\mu$l $LTB:bINH\alpha_c^{1-14}$ or LTB in PBS (0.01M phosphate buffer, pH 7.4 containing 0.15 M NaCl) was mixed with an equal volume of Freund's complete (primary injection) or incomplete (boosters) adjuvant (Calbiochem, La Jolla, Calif.) to give a final sample concentration of 10 or 40 $\mu$g $LTB:bINH\alpha_c^{1-14}$ or 40 $\mu$g LTB per 100 $\mu$l PBS. Antigen and adjuvant were mixed to give a stable emulsion as described for Example 3. For preparation of $LTB:bINH\alpha_c^{1-14}$ (10 or 40 $\mu$g/100 $\mu$l) or LTB (40 $\mu$g/100 $\mu$l) without Freund's adjuvant, samples were diluted in PBS and sterilized by expulsion through a 2.2 $\mu$m Millex GV sterile filter (Millipore, Bedford, Mass.) attached to a 5 ml syringe into a 15 ml sterile polypropylene tube.

Mice injected every 2 weeks received a primary injection of 10 or 40 $\mu$g $LTB:bINH\alpha_c^{1-14}$ or 40 $\mu$g LTB either in Freund's complete adjuvant or PBS followed by four subsequent boosters in Freund's incomplete or PBS. Mice injected every 4 weeks received a total of two boosters in 8 weeks. Control groups immunized against pentarneric or monomeric LTB (40 $\mu$g/mouse) were injected using the 2-week injection paradigm only.

At 68 days of age, 6 weeks after the first injection (two boosters for 20 week and one booster for 4-week interval), mice were anesthetized with Metofane, bled from the orbital sinus, and plasma collected as described above. Two weeks after the final booster, at 96 days of age, all mice were anesthetized with Metofane, body weight taken, and blood collected by heart puncture as described for Example 3. Blood samples (500 to 1,500 $\mu$l/mouse) were incubated at room temperature for 2 hours and then at 4° C. overnight, and serum was separated from clotted blood cells by centrifugation at 1000×g (Beckman GPR centrifuge) for 30 minutes at 4° C. and stored at–20° C. until assayed. After bleeding, testis, epididymis, seminal vesicle, heart, kidney, liver and spleen for each mouse were weighed.

Antibody Titer Determination

I. Pentameric EtxB Antibody Titer

Probind microliter plates (Falcon, Lincoln Park, N.J.) were coated overnight at room temperature with 0.2 $\mu$g/well GM1 in PBS followed by incubation with 100 ng/well pentameric LTB. After blocking non-specific binding sites with 1% bovine serum albumin (BSA) dissolved in PBS-T, the ELISA plates were incubated with mouse serum diluted 1:5000 in PBS-T containing 0.1% BSA (PBS-T-B, 1 hour), horseradish peroxidase-labeled goat anti-rabbit IgG (GAM0HRP, 1 hour; Vector, Burlingame, Calif.) diluted 1:5000 in PBS-T-B, then ortho-phenylenediamine in 0.1M citrate buffer, pH 4.5, containing 0.01% $H_xO_2$ (OPD-$H_2O_2$) as described in Example 4. Titer=$A_{490}$.

Monomeric EtxB Antibody Titer

Xenobind microliter plates (Xenopore Inc., Hawthorne, N.J.) were incubated with 200 ng/well monomeric LTB in PBS overnight (room temperature) to covalently link antigen to ELISA plate wells, as recommended by the manufacturer. After blocking non-specific binding sites with 3% gelatin in IIBS-T, ELISA plates were incubated with mouse serum diluted 1:5000 in PBS-T-B (1 hour), GAM-HRP (1 hour), then OPD-$H_2O_2$, as described for Example 4. Titer=$A_{490}$.

Inhibin Antibody Titer

Xenobind microliter plates were incubated with 1 μg/well $bINH\alpha_c^{1-26}$gly.tyr. or 1 μg/well partially purified bovine inhibin (ppbINH) in PBS overnight (room temperature) to covalently link antigen to ELISA plate wells, as recommended by the manufacturer. After blocking non-specific binding sites with 3% gelatin in PBS-T, ELISA plates were incubated with mouse plasma or serum diluted 1:100 in PBS-T-B (2 hours), GAM-HRP (1 hour), then OPD-$H_2O_2$, as described for Example 4. Titer=$A_{490}$.

FSH and LH RIA

Concentrations of FSH or LH in serum or plasma were determined in duplicate samples in RIA, as described for Example 4. Samples were analyzed in a single assay for each hormone. rFSH and rLH assay sensitivities were 0.625 and 0.156 ng/ml and intra-assay coefficients of variation (cv) were 6.3 and 1.6%, respectively. The cross reaction of FSH with LH and LH with FSH is <2% (per NIDDK guidelines).

Testosterone RIA

Concentrations of testosterone in serum were determined using the Coat-A-Count Total Testosterone assay kit from Diagnostic Products (DPC, Los Angeles, Calif.), per manufacturer's instruction for a non-extraction assay. Briefly, 50 μl of mouse serum was incubated with 1 ml tracer in antiserum-coated tubes at 37° C. for 3 hours. The coated tubes were decanted, and radioactivity bound to the dried tubes determined in a MACC Micromedic γ-counter. All samples were analyzed in a single assay. Assay sensitivity was 0.2 ng/ml and intraassay CV was 1.2%. The cross reactivities are: estradiol=0.02%; 5α-dihydrotestosterone= 3.4%; and other steroids=<1% (per DPC guidelines).

Statistics

Results were subjected to ANOVA. Whether significant ($P<0.05$) differences existed between means was determined by Student's t-test.

Results

Figure 7:
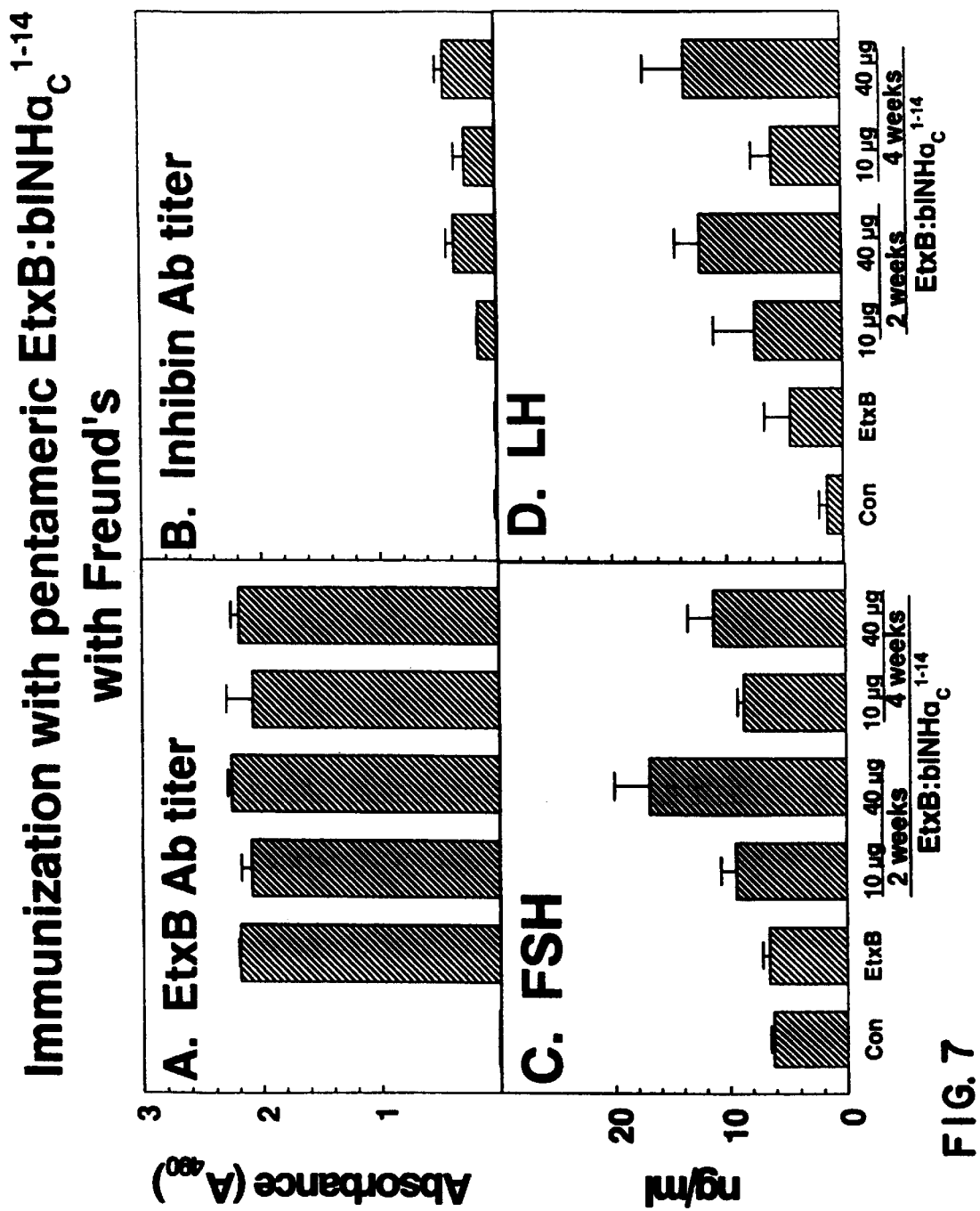
FIGS. 7A–7D are graphs showing antibody titers in mice actively immunized with monomeric LTB-inhibin fusion protein.

As shown in FIGS. 7 and 8, active immunization of animals with either the monomeric or pentameric form of the fusion protein LTB:$bINH\alpha_c^{1-14}$ with Freund's adjuvant resulted in increased anti-inhibin antibody titers as compared with the LTB control, and also resulted in increased levels of FSH and LH. Testosterone levels were decreased (data not shown). In contrast, active immunization with the fusion protein in the absence of adjuvant failed to alter anti-inhibin antibody titers or reproductive hormone levels.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A fusion protein comprising:
   beta subunit of heat labile enterotoxin from *E. coli* (LTB); and
   a peptide antigen of about 8 to 30 amino acids,
   wherein the peptide antigen is inserted into the amino acid sequence of LTB at a position within amino acids 50–61 without loss of LTB sequences; and
   wherein the fusion protein is immunoreactive with anti-inserted peptide antigen antibodies.

2. The fusion protein of claim 1, wherein the peptide antigen is inserted into an LTB sequence encoded by etxB at a position within nucleotides 229–260.

3. The fusion protein of clam 2, wherein the peptide antigen is inserted into the LTB sequence encoded by etxB at about nucleotide 237.

4. The fusion protein of clam 3, wherein the peptide antigen is inserted into the LTB sequence encoded by etxB at a unique Sma I site.

5. The fusion protein of claim 2, wherein said beta subunit of heat labile enterotoxin comprises a monomer or pentamer.

6. The fusion protein of claim 2, wherein said antigenic peptide is a bovine inhibin alpha-C subunit antigen comprising at least the first 14 amino acids of the N-terminus of the alpha-C subunit.

7. The fusion protein of claim 6, wherein the antigenic peptide comprises at least the first 24 amino acids of the N-terminus of the alpha-C subunit.

8. A composition comprising the fusion protein of claim 1 and an adjuvant.

9. A composition comprising the fusion protein of claim 6 and an adjuvant.

10. A vaccine comprising the composition of claim 8.

11. A vaccine comprising the composition of claim 9.

12. A multiple-antigen vaccine comprising:
    pentameric beta subunit of beat labile enterotoxin from *E. coli* (LTB) having multiple exposed surfaces;
    one or more peptide antigens inserted into one or more of the multiple exposed surfaces, wherein at least one of the one or more peptide antigens is inserted into the amino acid sequence of LTB at a position within amino acids 50–61 without loss of LTB sequences; and
    wherein the fusion protein is immunoreactive with anti-inserted peptide antigen antibodies.

13. The multiple-antigen vaccine of claim 12, wherein said at least one peptide antigen is a bovine inhibin alpha-C subunit antigen comprising at least the first 14 amino acids of the N-terminus of the alpha-C subunit.

14. A method of inducing an immune response in an animal against a desired protein, comprising the steps of:
    administering to the animal a fusion protein comprising:
      beta subunit of heat labile enterotoxim from *E. coli* (LTB); and
      a peptide antigen of about 8 to 30 amino acids,
      wherein te peptide antigen is inserted into amino acid sequence of LTB at a position within amino acids 50–61 without loss of LTB sequences; and
      wherein the fusion protein is immunoreactive with anti-inserted peptide antigen antibodies.

15. The method of claim 14, wherein the fusion protein administered comprises peptide antigen inserted into an LTB sequence encoded by extB at a position within nucleotides 229–260.

16. The method of claim 15 wherein the fusion protein administered comprises peptide antigen inserted into the LTB sequence encoded by etxB at about nucleotide 237.

17. The method of claim 16, wherein the fusion protein administered comprises peptide antigen inserted to the LTB sequence encoded by etxB at a unique Sma I site.

18. The method of claim 14, wherein the fussion protein administered comprises a monomer or pentamer of beta subunit of heat labile enterotoxin.

19. The method of claim 14, wherein the fusion protein administered comprises at least the first 14 amino acids of the N-terminus of the bovine inhibin alpha-C subunit.

20. The method of claim 19, wherein the fusion protein administered comprises at least the first 24 amino acids of the N-terminus of the alpha-C subunit.

21. A method for inducing an immune response in an animal against a desired protein, comprising the steps of:
   administering to the animal a fusion protein comprising:
      beta subunit of heat labile enterotoxin from *E. coli* (LTB); and
      a peptide antigen of about 8 to 30 amino acids,
   wherein the peptide antigen is inserted into the amino acid sequence of LTB at a position within amino acids 50–61 without loss of LTB sequences; and
   wherein the desired protein is inhibin, the peptide antigen is the first 14 N-terminal amino acids of the C-terminal portion of the alpha subunit of bovine inhibin, and wherein the fusion protein is immunoreactive with an anti-inhibin antibody.

* * * * *

UNITED STATES PATENT AND TRADEMARK OFFICE
CERTIFICATE OF CORRECTION

PATENT NO. : 5,993,820

DATED : NOVEMBER 30, 1999

INVENTOR(S): BAGDASARIAN ET AL.

It is certified that error appears in the above-identified patent and that said Letters Patent is hereby corrected as shown below:

Col. 2, line 7: "etxcB" should read --etxB--

Col. 3, line 10: "ei-terotoxin" should read --enterotoxin--

Col. 4, line 6: "niucleic" should read --nucleic--

Col. 7, line 11: insert --the two-- before the word "adenine"

Col. 7, lines 25-26: "Type LTB" should read --type LTB--

Col. 7, line 44: "*BacterioL*" should read --*Bacteriol*--

Col. 9, line 9: "(*E*" should read --(*V*--

Col. 9, line 10: "TRHY" should read --TRH--

Col. 10, line 8: "Pharinacia" should read --Pharmacia--

Col. 10, line 52: "bINH$\alpha_{c1-26}$" should read -- bINH$\alpha_c^{1-26}$--

Col. 14, line 37: "Bearner" should read --Beamer--

Col. 16, line 9: "40 pg" should read --40 µg--

UNITED STATES PATENT AND TRADEMARK OFFICE
CERTIFICATE OF CORRECTION

PATENT NO. : 5,993,820

DATED : NOVEMBER 30, 1999

INVENTOR(S) : BAGDASARIAN ET AL.

It is certified that error appears in the above-identified patent and that said Letters Patent is hereby corrected as shown below:

Col. 27, line 42, claim 3: "clam" should read --claim--

Col. 27, line 45, claim 4: "clam" should read --claim--

Col. 28, line 46, claim 14: "te" should read --the--

Col. 28, line 53, claim 15: "extB" should read --etxB--

Signed and Sealed this

Twenty-second Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 587 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 16...387
        (D) OTHER INFORMATION:

(xi) SEQUENCE DESCRIPTION: SEQ ID NO:1:

```
AATTCGGGAT GAATT ATG AAT AAA GTA AAA TTT TAT GTT TTA TTT ACG GCG        51
                Met Asn Lys Val Lys Phe Tyr Val Leu Phe Thr Ala
                 1               5                  10

TTA CTA TCC TCT CTA TGT GCA CAC GGA GCT CCT CAG TCT ATT ACA GAA        99
Leu Leu Ser Ser Leu Cys Ala His Gly Ala Pro Gln Ser Ile Thr Glu
```

```
           15                  20                  25
CTA TGT TCG GAA TAT CAC AAC ACA CAA ATA TAT ACG ATA AAT GAC AAG       147
Leu Cys Ser Glu Tyr His Asn Thr Gln Ile Tyr Thr Ile Asn Asp Lys
        30                  35                  40

ATA CTA TCA TAT ACG GAA TCG ATG GCA GGC AAA AGA GAA ATG GTT ATC       195
Ile Leu Ser Tyr Thr Glu Ser Met Ala Gly Lys Arg Glu Met Val Ile
45                  50                  55                  60

ATT ACA TTT AAG AGC GGC GCA ACA TTT CAG GTC GAA GTC CCG GGC AGT       243
Ile Thr Phe Lys Ser Gly Ala Thr Phe Gln Val Glu Val Pro Gly Ser
                65                  70                  75

CAA CAT ATA GAC TCC CAA AAA AAA GCC ATT GAA AGG ATG AAG GAC ACA       291
Gln His Ile Asp Ser Gln Lys Lys Ala Ile Glu Arg Met Lys Asp Thr
            80                  85                  90

TTA AGA ATC ACA TAT CTG ACC GAG ACC AAA ATT GAT AAA TTA TGT GTA       339
Leu Arg Ile Thr Tyr Leu Thr Glu Thr Lys Ile Asp Lys Leu Cys Val
        95                  100                 105

TGG AAT AAT AAA ACC CCC AAT TCA ATT GCG GCA ATC AGT ATG GAA AAC TA   389
Trp Asn Asn Lys Thr Pro Asn Ser Ile Ala Ala Ile Ser Met Glu Asn
    110                 115                 120

GTTTGCTTTA AAAGCATGTC TAATGCTAGG AACCTATATA ACAACTACTG TACTTATACT     449

AATGAGCCTT ATGCTGCATT TGAAAAGGCG GTAGAGGATG CAATACCGAT CCTTAAACTG     509

TAACACTATA ACAGCTTCCA CTACAGGGAG CTGTTATAGC AAACAGAAAA AACTAAGCTA     569

GGCTGGGGGG GCAAGCTT                                                   587
```

(2) INFORMATION FOR SEQ ID NO:2:

(i) SEQUENCE CHARACTERISTICS:
    (A) LENGTH: 124 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Met Asn Lys Val Lys Phe Tyr Val Leu Phe Thr Ala Leu Leu Ser Ser
1               5                   10                  15

Leu Cys Ala His Gly Ala Pro Gln Ser Ile Thr Glu Leu Cys Ser Glu
                20                  25                  30

Tyr His Asn Thr Gln Ile Tyr Thr Ile Asn Asp Lys Ile Leu Ser Tyr
            35                  40                  45

Thr Glu Ser Met Ala Gly Lys Arg Glu Met Val Ile Ile Thr Phe Lys
        50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
                100                 105                 110

Thr Pro Asn Ser Ile Ala Ala Ile Ser Met Glu Asn
            115                 120
```

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...39
        (D) OTHER INFORMATION:

(xi) SEQUENCE DESCRIPTION: SEQ ID NO:3:

```
GCT CCT CAG TCT ATT ACA GAA CTA TGT TCG GAA TAT CAC         39
Ala Pro Gln Ser Ile Thr Glu Leu Cys Ser Glu Tyr His
1               5                   10
```

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

```
Ala Pro Gln Ser Ile Thr Glu Leu Cys Ser Glu Tyr His
1               5                   10
```

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...39
        (D) OTHER INFORMATION:

(xi) SEQUENCE DESCRIPTION: SEQ ID NO:5:

```
GCT CCT CAG TCT ATT ACA GAT CTA TGT TCG GAA TAT CAC         39
```

```
Ala Pro Gln Ser Ile Thr Asp Leu Cys Ser Glu Tyr His
1               5                   10
```

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

```
Ala Pro Gln Ser Ile Thr Asp Leu Cys Ser Glu Tyr His
1               5                   10
```

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...31
        (D) OTHER INFORMATION:

(xi) SEQUENCE DESCRIPTION: SEQ ID NO:7:

```
ATG GCA GGC AAA AGA GAA ATG GTT ATC ATT A           31
Met Ala Gly Lys Arg Glu Met Val Ile Ile Il
1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE:

(iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

```
Xaa Xaa Gly Lys Arg Glu Met Val Ile Ile Ile
1               5                   10
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...31
        (D) OTHER INFORMATION:

(xi) SEQUENCE DESCRIPTION: SEQ ID NO:9:

```
ATG GCA GGC CTA AGA GAA ATG GTT ATC ATT A                    31
Met Ala Gly Leu Arg Glu Met Val Ile Ile Il
 1               5                   10
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

```
Met Ala Gly Leu Arg Glu Met Val Ile Ile Ile
 1               5                   10
```

(2) INFORMATION FOR SEQ ID NO:11:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...31
        (D) OTHER INFORMATION:

(xi) SEQUENCE DESCRIPTION: SEQ ID NO:11:

-continued

```
GTC GAA GTC CCT GGA TCC ACC CCG CCG CTG C CGTGGCCGTG GTCCCCGGCT GC    53
Val Glu Val Pro Gly Ser Thr Pro Pro Leu Pro
1               5                   10

TCTGGGCAGT CAA                                                       66

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

Val Glu Val Pro Gly Ser Thr Pro Pro Leu Pro
1               5                   10
```